United States Patent [19]

Ueda et al.

[11] 4,309,437
[45] Jan. 5, 1982

[54] PYRROLO-BENZODIAZEPINE COMPOUNDS AND ANTI-TUMOR COMPOSITION THEREOF

[75] Inventors: Yasuo Ueda, Hirakata; Yoshio Kagitani, Kashiwara; Eiji Sako, Osaka; Tadakazu Suyama, Ianabemachi; Nobuhiko Komatsu, Tokyo; Daisuke Satoh, Nishinomiya, all of Japan

[73] Assignee: The Green Cross Corporation, Kyoto, Japan

[21] Appl. No.: 127,984

[22] Filed: Mar. 4, 1980

[30] Foreign Application Priority Data

Jul. 17, 1979 [JP] Japan .................................. 54-89886

[51] Int. Cl.³ ...................... A61K 31/55; C07D 487/04
[52] U.S. Cl. .............................. 424/274; 260/239.3 T

[58] Field of Search .................. 260/239.3 T; 424/274

[56] References Cited

U.S. PATENT DOCUMENTS 3,523,941  8/1970  Leimgruber et al. ........ 260/239.3 T
3,524,849  8/1970  Batcho et al. ................ 260/239.3 T Primary Examiner—Henry R. Jiles
Assistant Examiner—Robert T. Bond
Attorney, Agent, or Firm—Cushman, Darby & Cushman

[57] ABSTRACT

Novel 5,10,11,11a-tetrahydro-8-methyl-11-sulfo or sulfino-1H-pyrrolo[2,1-c][1,4]-benzodiazepin-2-acrylamides which have antitumor activity and low toxicity are prepared by reacting corresponding 11-reactive compound with a reactive sulfur compound to form 11-sulfino compounds and, if desired, oxidizing the 11-sulfino compounds to obtain 11-sulfo compound.

28 Claims, No Drawings

PYRROLO-BENZODIAZEPINE COMPOUNDS AND ANTI-TUMOR COMPOSITION THEREOF

This invention relates to a novel compound and, more particularly, to a novel 1H-pyrrolo-[2,1-c][1,4]benzodiazepin-2-acrylamide compound having antitumor activity.

It has already been known antibacterial and antitumor activities are exhibited by the three compounds including 5,10,11,11a-tetrahydro-9,11-dihydroxy-8-methyl-5-oxo-1H-pyrrolo[2,1-c][1,4]-benzodiazepin-2-acrylamide (hereinafter referred to as "PBA") represented by the formula

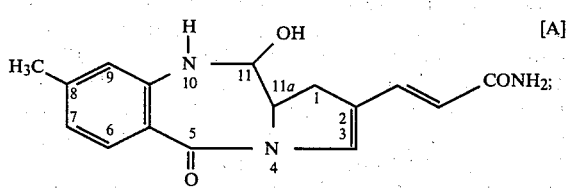

5,11,11a-trihydro-9-hydroxy-8-methyl-5-oxo-1H-pyrrolo- [2,1-c][1,4]benzodiazepin-2-acrylamide (hereinafter referred to as "P'B'A'") represented by the formula

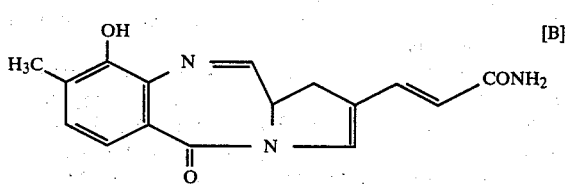

which formula corresponds to that of a compound derived from the former compound "PBA" by the removal of substituents at 10- and 11-position by the dehydration reaction; and a compound having a methyl ether group at 11-position of PBA (hereinafter referred to as "P"B"A''").

It has been disclosed that PBA is produced as metabolite on cultivating *Streptomyces spadicogriseus* KOMATSU, FERM P-3275, ATCC 31179 or *Streptomyces refuineus var. thermotolerans* NRRL 3143, NRRL 3144 and that P'B'A' and P"B"A" can be derived from PBA [Japanese Patent Application Laid-open No. 79,082/1977; U.S. Pat. No. 3,361,742; J. Amer. Chem. Soc., 87, 5791–5793 (1965)].

And also, it has already been known that compounds (PBA derivatives) represented by the formula:

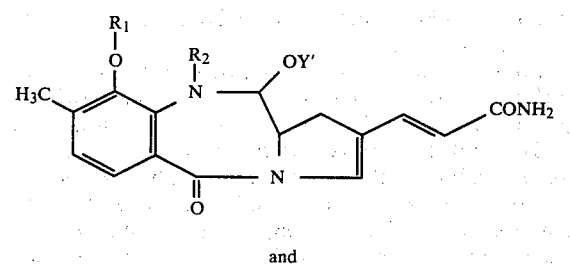

and

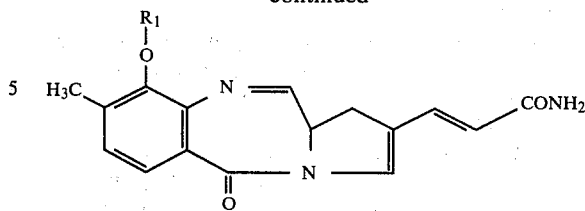

wherein $R_1$ is selected from the group consisting of hydrogen, acyl, carbamyl and alkoxycarbonyl; $R_2$ is selected from the group consisting of hydrogen and acyl; and at last one of $R_1$ and $R_2$ is a substituent other than hydrogen; Y' is selected from the group consisting of alkyl, hydrogen, phenylalkyl and acyl, $R_2$ and the group OY' taken together can be a chemical bond, display activity as antitumor agent [U.S. Pat. Nos. 3,523,941 and 3,524,849].

As has been known, although PBA, P'B'A' P"B"A" and the other PBA derivatives have very strong antitumor activity, they are said to exhibit strong toxicity, particularly cardiotoxicity, due to side effects. Consequently, in spite of their usefulness, they are subject to strict restriction in their use as therapeutic drugs. The present inventors, therefore, carried out extensive researches for the purpose of developing a compound in which the side effects of these compounds have been eliminated or diminished without causing significant decline in antitumor activity. Thus, various compounds were synthesized starting from PBA, P'B'A' and other PBA derivatives and subjected to screening tests with respect to antitumor activity and toxicity to explore novel compounds. As a result, the present invention has been accomplished.

The object of this invention is to provide a novel 1H-pyrrolo-[2,1-c][1,4]benzodiazepin-2-acrylamide compound having antitumor activity and low toxicity.

According to the present invention, there is provided a novel 1H-pyrrolo[2,1-c][1,4]benzodiazepin-2-acrylamide compound represented by the formula

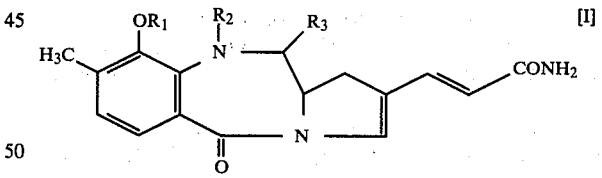

wherein $R_1$ represents a hydrogen atom, acyl group, carbamyl group, or alkoxycarbonyl group, $R_2$ represents a hydrogen atom or acyl group, and $R_3$ represents a sulfinic acid moiety ($SO_2X$) or sulfonic acid moiety ($SO_3X$), X being hydrogen or pharmaceutically acceptable cation.

In the compound above, acyl is benzoyl or alkanoyl having 1 to 6 carbon atoms; carbamyl may have its nitrogen atom substituted with a phenyl group or an alkyl group containing 1 to 6 carbon atoms; and alkoxycarbonyl contains alkoxy group having 1 to 6 carbon atoms.

Examples of the compounds represented by the formula [I] are given below.

5,10,11,11a-Tetrahydro-10-acetyl-9-hydroxy-8-methyl-5-oxo-11-sulfo-1H-pyrrolo[2,1-c][1,4]benzodiazepin- 2-acrylamine and alkali metal salts or alkaline earth metal salts thereof.

5,10,11,11a-Tetrahydro-9-acetoxy-10-acetyl-8-methyl-5-oxo-11-sulfo-1H-pyrrolo[2,1-c][1,4]benzodiazepin-2-acrylamide and alkali metal salts or alkaline earth metal salts thereof.

5,10,11,11a-Tetrahydro-10-acetyl-9-carbamyloxy-8-methyl-5-oxo-11-sulfo-1H-pyrrolo[2,1-c][1,4]benzodiazepin-2-acrylamide and alkali metal salts or alkaline earth metal salts thereof.

5,10,11,11a-Tetrahydro-9-hydroxy-8-methyl-5-oxo-11-sulfo-1H-pyrrolo[2,1-c][1,4]benzodiazepin-2-acrylamide and alkali metal salts or alkaline earth metal salts thereof.

5,10,11,11a-Tetrahydro-9-acetoxy-8-methyl-5-oxo-11-sulfo-1H-pyrrolo[2,1-c][1,4]benzodiazepin-2-acrylamide and alkali metal salts or alkaline earth metal salts thereof.

5,10,11,11a-Tetrahydro-9-carbamyloxy-8-methyl-5-oxo-11-sulfo-1H-pyrrolo[2,1-c][1,4]benzodiazepin-2-acrylamide and alkali metal salts or alkaline earth metal salts thereof.

5,10,11,11a-Tetrahydro-10-acetyl-9-hydroxy-8-methyl-5-oxo-11-sulfino-1H-pyrrolo[2,1-c][1,4]-benzodiazepin-2-acrylamide and alkali metal salts or alkaline earth metal salts thereof.

5,10,11,11a-Tetrahydro-9-acetoxy-10-acetyl-8-methyl-5-oxo-11-sulfino-1H-pyrrolo[2,1-c][1,4]-benzodiazepin-2-acrylamide and alkali metal salts or alkaline earth metal salts thereof.

5,10,11,11a-Tetrahydro-10-acetyl-9-carbamyl-8-methyl-5-oxo-11-sulfino-1H-pyrrolo[2,1-c][1,4]-benzodiazepin-2-acrylamide and alkali metal salts or alkaline earth metal salts thereof.

5,10,11,11a-Tetrahydro-9-hydroxy-8-methyl-5-oxo-11-sulfino-1H-pyrrolo[2,1-c][1,4]benzodiazepin-2-acrylamide and alkali metal salts or alkaline metal salts thereof.

5,10,11,11a-Tetrahydro-9-acetoxy-8-methyl-5-oxo-11-sulfino-1H-pyrrolo[2,1-c][1,4]benzodiazepin-2-acrylamide and alkali metal salts or alkaline earth metal salts thereof.

5,10,11,11a-Tetrahydro-9-carbamyloxy-8-methyl-5-oxo-11-sulfino-1H-pyrrolo[2,1-c][1,4]benzodiazepin-2-acrylamide and alkali metal salts or alkaline earth metal salts thereof.

5,10,11,11a-Tetrahydro-8-methyl-9-methoxycarbonyloxy-5-oxo-11-sulfo-1H-pyrrolo[2,1-c][1,4]-benzodiazepin-2-acrylamide and alkali metal salts or alkaline earth metal salts thereof.

Of the compounds of this invention, those having a sulfinic acid moiety or a salt thereof as $R_3$ of the formula [I] are obtained by allowing a reactive sulfur compound to react in an inert solvent with PBA or its derivatives represented by the formula

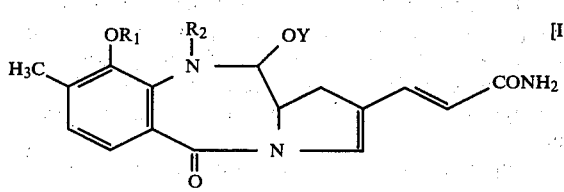

or

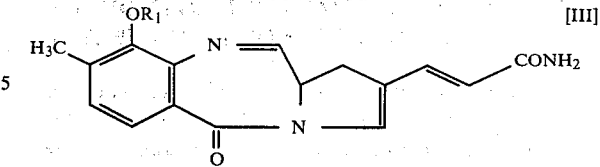

wherein $R_1$ and $R_2$ are the same as those described above and Y represents a hydrogen atom, an alkyl group or a phenyl(lower)alkyl group.

Examples of the inert solvents include an organic solvent such as methanol, ethanol, acetone, dimethylformamide, dimethyl sulfoxide, diethyl ether, benzene and hexane, which may contain water if necessary. Suitable reactive sulfur compounds include, for example, disulfurous acid, trithionic acid, dithionic acid, dithionous acid, sulfurous acid, alkali metal or alkaline earth metal salts thereof, and sulfur dioxide. These sulfur compounds are used either directly or in the form of solution or suspension in water or organic solvents. It is also feasible to allow a suitable reducing agent (e.g. zinc dust) and sulfurous acid to react with a compound of the formula [II] or [III]. In any case, the reaction proceeds sufficiently at a temperature near room temperature. After completion of the reaction, the intended product may be isolated from the reaction mixture by common physical and chemical means such as concentration, precipitation and chromatography, while keeping the product from oxidation under a nitrogen stream or by other means.

The 11-sulfino derivatives of this invention obtained by the above procedures using the starting compounds of formula [II] or formula [III] in which $R_1$, $R_2$ and Y are can also be all or partly hydrogen atom, converted by common procedures into 11-sulfino derivatives of the present invention, which have the defined substituents other than hydrogen atom for $R_1$ and $R_2$, respectively, in the formula [I].

Of the compounds of this invention, those having a sulfonic acid moiety or a salt thereof as R of the formula [I] are easily obtained from the above 11-sulfino derivatives by common oxidation techniques such as passing an oxygen or molecular oxygen containing gas such as air stream through a solution of the sulfino derivative.

The results of toxicity tests and antitumor activity tests performed to confirm the usefulness of the compounds of this invention were as shown in Table 1. The tests were performed in the following way.

Toxicity test: The compound being tested is suspended in physiological saline in varied concentrations by the serial dilution method (common ratio, 1:1.5). Each solution was administered intraperitoneally to groups of 8 to 12 dd-strain male mice, each 18 to 21 g in body weight. The mice were then bred on a usual diet and water. The $LD_{50}$ value was determined by Probit analysis by observing dead and alive for 3 weeks after the administration.

Antitumor activity test: Leukemia P388, $10^6$ cells in number, were inoculated into each member of the groups of 8 to 12 $CDF_1$-strain male mice, 18 to 20 g in body weight. The compound under test was intraperitoneally administered to the groups being treated in predetermined doses for 6 consecutive days after 24 hours from the inoculation. The days elaspsed untill death of the test animal were counted for each mouse to obtain average survival days. The prolongation of survival time, indicative of the effectiveness of a test compound, was calculated by the following equation:

Prolongation of survival time, % = 
$$\frac{\text{Average survival days of the group being treated}}{\text{Average survival days of the control group}} \times 100$$

TABLE 1

Toxicity and antitumor activity of the compounds represented by the general formula [I].

| | | | | Animal test | |
|---|---|---|---|---|---|
| $R_1$ at 9-position | $R_2$ at 10-position | $R_3$ at 11-position | $LD_{50}$ (mg/kg) | Daily dose* (mg/kg) | Prolongation of survival time, % |
| H | H | $SO_2H$ | 2.18 | 0.12 | 212.0 |
| $COCH_3$ | H | $SO_2H$ | 2.54 | 0.12 | 210.0 |
| $CONH_2$ | H | $SO_2H$ | 2.37 | 0.12 | 200.3 |
| $COOCH_3$ | H | $SO_2H$ | 2.56 | 0.12 | 198.7 |
| H | $COCH_3$ | $SO_2H$ | 2.50 | 0.12 | 233.3 |
| $COCH_3$ | $COCH_3$ | $SO_2H$ | 2.62 | 0.12 | 190.0 |
| $CONH_2$ | $COCH_3$ | $SO_2H$ | 2.84 | 0.12 | 201.3 |
| H | H | $SO_3H$ | 2.21 | 0.12 | 213.1 |
| $COCH_3$ | H | $SO_3H$ | 2.68 | 0.12 | 213.3 |
| $CONH_2$ | H | $SO_3H$ | 2.40 | 0.12 | 217.1 |
| $COOCH_3$ | H | $SO_3H$ | 2.55 | 0.12 | 206.7 |
| H | $COCH_3$ | $SO_3H$ | 2.43 | 0.12 | 198.6 |
| $COCH_3$ | $COCH_3$ | $SO_3H$ | 2.81 | 0.12 | 193.3 |
| $CONH_2$ | $COCH_3$ | $SO_3H$ | 2.80 | 0.12 | 197.2 |
| H | H | $SO_2Na$ | 2.28 | 0.12 | 209.2 |
| H | H | $SO_2K$ | 2.31 | 0.12 | 208.6 |
| $COCH_3$ | H | $SO_2Na$ | 2.60 | 0.12 | 199.6 |
| H | H | $SO_3Na$ | 2.31 | 0.12 | 209.9 |
| H | $COCH_3$ | $SO_3Na$ | 2.51 | 0.12 | 216.4 |
| $COCH_3$ | $COCH_3$ | $SO_2Na$ | 2.71 | 0.12 | 200.0 |
| $COCH_3$ | $COCH_3$ | $SO_3Na$ | 3.04 | 0.12 | 201.0 |
| | PBA | | 0.73 | 0.12 | 216.7 |

Note:-
Daily dose* was expresed in terms of PBA {5,10,11,11a-tetrahydro-5,11-dihydroxy-8-methyl-1H-pyrrolo[2,1-c][1,4]benzodiazepin-2-acrylamide}.

EXAMPLE 1

In 200 ml of methanol, was dissolved 2 g of 5,10,11,11a-tetrahydro-10-acetyl-9-hydroxy-8-methyl-11-methoxy-5-oxo-1H-pyrrolo[2,1-c][1,4]benzodiazepin-2-acrylamide. The resulting solution was mixed with a solution containing 20 g of sodium dithionate in 1,800 ml of water. The mixture was stirred at 20° to 35° C. for one hour and then admixed with 2,000 ml of n-butanol with thorough stirring. The butanol layer was separated, dried over anhydrous sodium sulfate and evaporated to dryness. The residue was dissolved in 200 ml of methanol, then, admixed with 800 ml of chloroform and applied to the top of a silica gel column (40×1,000 mm). The adsorbed phase was developed with a methanol-chloroform (1:4) mixture and the fraction containing the intended substance was confirmed by the bioautogram (*Staphylococcus aureus*) using thin layer chromatography [developing solvent: an ethyl acetate-methanol (4:1) mixture]. The effective fraction was dried over anhydrous sodium sulfate, concentrated in vacuo and the crystalline substance was collected by filtration under a nitrogen stream. This substance was recrystallized from methanol to obtain 1.75 g of yellow needle crystals of 5,10,11,11a-tetrahydro-10-acetyl-9-hydroxy-8-methyl-5-oxo-11-sulfino-1H-pyrrolo[2,1-c][1,4]benzodiazepin-2-acrylamide sodium salt melting at 253.7°–256.7° C., which was a compound of the formula [I].

Elementary analysis: Calculated for $C_{18}H_{18}N_3O_6S_1Na$: C, 50.58; H, 4.24; N, 9.83; S, 7.50; Na, 5.38. Found: C, 51.24; H, 4.29; N, 9.59; S, 7.61; Na, 5.30.

Infrared absorption spectrum: 1670, 1410, 1220, 1040 $cm^{-1}$.

EXAMPLE 2

In 100 ml of methanol, was dissolved 1 g of 5,10,11,11a-tetrahydro-9-acetoxy-10-acetyl-11-methoxy-8-methyl-5-oxo-1H-pyrrolo[2,1-c][1,4]benzodiazepin-2-acrylamide. The resulting solution was mixed with a solution containing 20 g of sodium dithionite in 1,800 ml of water. The mixture was stirred at 30° to 45° C. for 30 minutes and then admixed with 2,000 ml of n-butanol with thorough stirring. The butanol layer was separated and concentrated. When a greater part of the butanol had been evaporated, the residue was again dissolved in water and applied to the top of an Amberlite XAD-2 column (40×100 mm). The column was then eluted with a methanolwater (8:2) mixture. After having been confirmed by thin layer chromatography as in Example 1, the fraction containing the intended product was separated and evaporated in vacuo to dryness. The residue was recrystallized from an ethanol-benzene mixture to obtain 0.8 g of yellow needle crystals of 5,10,11,11a-tetrahydro-9-acetoxy-10-acetyl-8-methyl-5-oxo-11-sulfino-1H-pyrrolo-[2,1-c][1,4]benzodiazepin-2-acrylamide melting at 241.3°–245.1° C., which was a compound of the formula [I].

Elementary analysis: Calculated for $C_{20}H_{21}N_3O_7S_1$: C, 53.68; H, 4.73; N, 9.39; S, 7.16. Found: C, 52.95; H, 4.68; N, 9.21; S, 7.01.

Infrared absorption spectrum: 1690, 1400, 1210, 1035 $cm^{-1}$.

EXAMPLE 3

In 200 ml of methanol, was dissolved 2 g of 5,10,11,11a-tetrahydro-10-acetyl-9-hydroxy-8-methyl-11-methoxy-5-oxo-1H-pyrrolo[2,1-c][1,4]benzodiazepin-2-acrylamide. The resulting solution was mixed with a solution containing 20 g of sodium dithionate in 1,800 ml of water. The mixture was stirred at 20° to 35° C. for one hour and then admixed with 2,000 ml of n-butanol with thorough stirring. The butanol layer was separated, dried over anhydrous sodium sulfate and evaporated to dryness. The residue was recrystallized from a methanol-benzene mixture, then again from methanol to obtain 0.7 g of yellow needle crystals, of 5,10,11,11a-tetrahydro-10-acetyl-9-hydroxy-8-methyl-5-oxo-11-sulfino-1H-pyrrolo-[2,1-c][1,4]benzodiazepin-2-acrylamide melting at 249.6°–253.2° C., which was a compound of the formula [I].

Elementary analysis: Calculated for $C_{18}H_{19}N_3O_6S_1$: C, 53.33; H, 4.72; N, 10.36; S, 7.91. Found: C, 52.95; H, 4.68; N, 10.62; S, 8.00.

Infrared absorption spectrum: 1700, 1410, 1200, 1040 $cm^{-1}$.

EXAMPLE 4

In a manner similar to that in Example 2, 1 g of 5,10,11,11a-tetrahydro-10-acetyl-9-carbamyloxy-11-methoxy-8-methyl-5-oxo-1H-pyrrolo[2,1-c][1,4]benzodiazepin-2acrylamide was treated to obtain 0.65 g of pale yellow needle crystals of 5,10,11,11a-tetrahydro-10-acetyl-9-carbamyloxy-8-methyl-5-oxo-11-sulfino-1H-pyrrolo[2,1-c][1,4]benzodiazepin-2-acrylamide melting at 210.1°–211.9° C., which was a compound of the formula [I].

Elementary analysis: Calculated for $C_{19}H_{20}N_4O_7S_1$: C, 50.89; H, 4.50; N, 12.50; S, 7.15. Found: C, 50.70; H 4.33; N, 12.45; S, 7.08.

Infrared absorption spectrum: 1690, 1400, 1210, 1030 cm$^{-1}$.

EXAMPLE 5

In a manner similar to that in Example 3, 2 g of 5,11,11a-trihydro-9-hydroxy-8-methyl-5-oxo-1H-pyrrolo[2,1-c][1,4]benzodiazepin-2-acrylamide was treated to obtain 1.82 g of white or pale yellow needle crystals of 5,10,11,11a-tetrahydro-9-hydroxy-8-methyl-5-oxo-11-sulfino-1H-pyrrolo[2,1-c][1,4]-benzodiazepin-2-acrylamide melting at 251.6°–255.3° C., which was a compound of the formula [I].

Elementary analysis: Calculated for $C_{16}H_{17}N_3O_5S_1$: C, 52.88; H, 4.72; N, 11.56; S, 8.82. Found: C, 52.70; H, 4.69; N, 11.80; S, 8.79.

Infrared absorption spectrum: 1620, 1410, 1210, 1040 cm$^{-1}$.

EXAMPLE 6

In a manner similar to that in Example 1, 2 g of 5,10,11,11a-tetrahydro-9-acetoxy-11-hydroxy-8-methyl-5-oxo-1H-pyrrolo[2,1-c][1,4]benzodiazepin-2-acrylamide was treated to obtain 1.65 g of pale yellow needle crystals of 5,10,11,11a-tetrahydro-9-acetoxy-8-methyl-5-oxo-11-sulfino-1H-pyrrolo[2,1-c][1,4]benzodiazepin-2-acrylamide sodium salt melting at 211.2°–213.5° C., which was a compound of the formula [I].

Elementary analysis: Calculated for $C_{18}H_{18}N_3O_6S_1Na$: C, 50.60; H, 4.25; N, 9.83; S, 7.50; Na, 5.38. Found: C, 50.30; H, 4.31; N, 9.84; S, 7.70; Na, 5.42.

Infrared absorption spectrum: 1640, 1410, 1200, 1090 cm$^{-1}$.

EXAMPLE 7

In a manner similar to that in Example 1, 2 g of 5,10,11,11a-tetrahydro-9-carbamyloxy-11-methoxy-8-methyl-5-oxo-1H-pyrrolo[2,1-c][1,4]benzodiazepin-2-acrylamide was treated to obtain 1.28 g of pale yellow needle crystals of 5,10,11,11a-tetrahydro-9-carbamyloxy-8-methyl-5-oxo-11-sulfino-1H-pyrrolo[2,1-c][1,4]benzodiazepin-2-acrylamide sodium salt melting at 216.3°–219.2° C., which was a compound of the formula [I].

Elementary analysis: Calculated for $C_{17}H_{17}N_4O_6S_1Na$: C, 47.66; H, 4.00; N, 13.08; S, 7.48; Na, 5.37. Found: C, 47.78; H, 3.99; N, 13.13; S, 7.43; Na, 5.30.

Infrared absorption spectrum: 1640, 1400, 1200, 1090 cm$^{-1}$.

EXAMPLE 8

5,10,11,11a-Tetrahydro-10-acetyl-9-hydroxy-8-methyl-11-methoxy-5-oxo-1H-pyrrolo[2,1-c][1,4]-benzodiazepin-2-acrylamide was treated in a manner similar to that in Example 1 to obtain 5,10,11,11a-tetrahydro-10-acetyl-9-hydroxy-8-methyl-5-oxo-11-sulfino-1H-pyrrolo[2,1-c][1,4]benzodiazepin-2-acrylamide sodium salt. A 2 g portion of this salt was dissolved in 250 ml of water and oxidized by passing air through the solution. After lyophilization, the oxidation mixture was dissolved in methanol, then admixed with a four-fold volume of chloroform and applied to the top of a silica gel column (40×100 mm). The loaded column was developed with a methanol-chloroform mixture. The fraction containing the intended product was concentrated in vacuo and recrystallized from methanol to obtain 1 g of yellow needle crystals of 5,10,11,11a-tetrahydro-10-acetyl-9-hydroxy-8-methyl-5-oxo-11-sulfo-1H-pyrrolo[2,1-c][1,4]benzodiazepin-2-acrylamide sodium salt melting at 261°–262.5° C., which was a compound of the formula [I].

Elementary analysis: Calculated for $C_{18}H_{18}N_3O_7S_1Na$: C, 48.76; H, 4.09; N, 9.48; S, 7.23; Na, 5.18. Found: C, 48.85; H, 4.11; N, 9.52; S, 7.18; Na, 5.10.

Infrared absorption spectrum: 1650, 1410, 1210, 1030 cm$^{-1}$.

EXAMPLE 9

In 200 ml of methanol, was dissolved 2 g of 5,10,11,11a-tetrahydro-9-acetoxy-11-methoxy-8-methyl-5-oxo-1H-pyrrolo[2,1-c][1,4]benzodiazepin-2-acrylamide. The resulting solution was stirred for 30 minutes, while being slowly passed through with a gaseous sulfur dioxide stream. After the reaction had been completed, the solution was admixed with 2,000 ml of n-butanol with thorough stirring, and the butanol layer was separated, dried over anhydrous sodium sulfate and evaporated to dryness. The dried residue was recrystallized from a methanol-benzene mixture and the crystals were again dissolved in 300 ml of methanol. An oxygen stream was slowly passed through the solution for about 40 minutes. The solution was then fractionated by means of an Amberlite XAD-2 column as in Example 2. The fraction containing the intended product was concentrated and recrystallized to obtain 1.62 g of yellow needle crystals of 5,10,11,11a-tetrahydro-9-acetoxy-8-methyl-5-oxo-11-sulfo-1H-pyrrolo[2,1-c][1,4]benzodiazepin-2-acrylamide melting at 231.4°–235.4° C., which was a compound of the formula [I].

Elementary analysis: Calculated for $C_{18}H_{19}N_3O_7S_1$: C, 51.3; H, 4.54; N, 9.97; S, 7.61. Found: C, 50.9; H, 4.62; N, 9.83; S, 7.55.

Infrared absorption spectrum: 1660, 1420, 1210, 1029 cm$^{-1}$.

EXAMPLE 10

In 200 ml of methanol, was dissolved 2 g of 5,10,11,11a-tetrahydro-10-acetyl-9-acetoxy-8-methyl-11-methoxy-5-oxo-1H-pyrrolo[2,1-c][1,4]benzodiazepin-2-acrylamide. The resulting solution was mixed with a solution containing 18 g of potassium sulfite in 1,800 ml of water. After addition of 2 g of zinc dust, the mixture was stirred at room temperature for about 4 hours. Then, the mixture was admixed with 2,000 ml of n-butanol and thoroughly stirred. The butanol layer was separated, dried over anhydrous sodium sulfate, and evaporated to dryness. The dried product was dissolved in a water-methanol (1:1) mixture. An oxygen stream was slowly passed through the solution for about 3 hours. In a manner similar to that in Example 2, the solution was fractionated by means of an Amberlite XAD-2 column to separate a fraction containing the intended product. This fraction was concentrated and recrystallized to obtain 1.23 g of yellow needle crystals of 5,10,11,11a-tetrahydro-9-acetoxy-10-actyl-8-methyl-5-oxo-11-sulfo-1H-pyrrolo[2,1-c][1,4]benzodiazepin-2-acrylamide potassium salt melting at 221.3°–223.7° C., which was a compound of the formula [I].

Elementary analysis: Calculated for $C_{20}H_{20}N_3O_8S_1K$: C, 47.90; H, 4.02; N, 8.38; S, 6.39; K, 7.80. Found: C, 47.77; H, 3.98; N, 8.41; S, 6.44; K, 7.75.

Infrared absorption spectrum: 1680, 1410, 1210, 1035 cm$^{-1}$.

EXAMPLE 11

5,10,11,11a-Tetrahydro-9-carbamyloxy-8-methyl-5-oxo-11-sulfino-1H-pyrrolo[2,1-c][1,4]benzodiazepin-2-acrylamide sodium salt was obtained as in Example 7. A 1 g portion of this salt was dissolved in 150 ml of water and treated in a manner similar to that in Example 8. On recrystallization from methanol, there was obtained 0.72 g of yellow needle crystals of 5,10,11,11a-tetrahydro-9-carbamyloxy-8-methyl-5-oxo-11-sulfo-1H-pyrrolo[2,1-c][1,4]benzodiazepin-2-acrylamide sodium salt melting at 241.6°–243.2° C., which was a compound of the formula [I].

Elementary analysis: Calculated for $C_{17}H_{17}N_4O_7S_1Na$: C, 45.95; H, 3.86; N, 12.61; S, 7.21; Na, 5.17. Found: C, 46.20; H, 4.05; N, 13.10; S, 7.17; Na, 5.08.

Infrared absorption spectrum: 1680, 1400, 1220, 1040 cm$^{-1}$.

EXAMPLE 12

A 2 g portion of 5,10,11,11a-tetrahydro-8-methyl-11-methoxy-9-methoxycarbonyloxy-5-oxo-1H-pyrrolo[2,1-c][1,4]benzodiazepin-2-acrylamide was treated as in Example 9 to obtain 1.37 g of pale yellow needle crystals of 5,10,11,11a-tetrahydro-8-methyl-9-methoxycarbonyloxy-5-oxo-11-sulfo-1H-pyrrolo[2,1-c][1,4]-benzodiazepin-2-acrylamide melting at 232.3°–236.8° C., which was a compound of the formula [I].

Elementary analysis: Calculated for $C_{18}H_{19}N_3O_8S_1$: C, 49.43; H, 4.38; N, 9.61; S, 7.33. Found: C, 50.10; H, 4.40; N, 9.65; S, 7.28.

Infrared absorption spectrum: 1620, 1415, 1220, 1030 cm$^{-1}$.

What is claimed is:

1. A 1H-pyrrolo[2,1-c][1,4]benzodiazepin-2-acrylamide compound represented by the formula

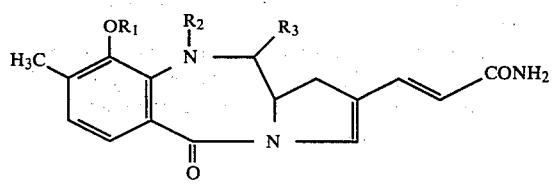

wherein $R_1$ represents a hydrogen atom, alkanoyl group having 1 to 6 carbon atoms, benzoyl group, phenylcarbamyl group, alkyl carbamyl group having 1 to 6 carbon atoms, or alkoxycarbonyl group wherein the alkoxy portion has 1 to 6 carbon atoms, $R_2$ represents a hydrogen atom, an alkanoyl group having 1 to 6 carbon atoms or a benzoyl group, and $R_3$ represents a sulfinic acid residue, $SO_2X$, or sulfonic acid residue, $SO_3X$, wherein X is hydrogen or a pharmaceutically acceptable cation.

2. The compound of claim 1, wherein $R_3$ in the formula [I] is sulfininic acid residue.

3. The compound of claim 1, wherein $R_3$ in the formula [I] is sulfonic acid residue.

4. The compound of claim 1, 2 or 3, wherein the pharmaceutically acceptable cation is alkali metal cation or an alkaline earth metal cation.

5. 5,10,11,11a-Tetrahydro-10-acetyl-9-hydroxy-8-methyl-5-oxo-11-sulfo-1H-pyrrolo[2,1-c][1,4]-benzodiazepin-2-acrylamide.

6. 5,10,11,11a-Tetrahydro-9-acetoxy-10-acetyl-8-methyl-5-oxo-11-sulfo-1H-pyrrolo[2,1-c][1,4]-benzodiazepin-2-acrylamide.

7. 5,10,11,11a-Tetrahydro-10-acetyl-9-carbamyloxy-8-methyl-5-oxo-11-sulfo-1H-pyrrolo[2,1-c][1,4]benzodiazepin-2-acrylamide.

8. 5,10,11,11a-Tetrahydro-9-hydroxy-8-methyl-5-oxo-11-sulfo-1H-pyrrolo[2,1-c][1,4]benzodiazepin-2-acrylamide.

9. 5,10,11,11a-Tetrahydro-9-acetoxy-8-methyl-5-oxo-11-sulfo-1H-pyrrolo[2,1-c][1,4]benzodiazepin-2-acrylamide.

10. 5,10,11,11a-Tetrahydro-9-carbamyloxy-8-methyl-5-oxo-11-sulfo-1H-pyrrolo[2,1-c][1,4]benzodiazepin-2-acrylamide.

11. 5,10,11,11a-Tetrahydro-10-acetyl-9-hydroxy-8-methyl-5-oxo-11-sulfino-1H-pyrrolo[2,1-c][1,4]-benzodiazepin-2-acrylamide.

12. 5,10,11,11a-Tetrahydro-9-acetoxy-10-acetyl-8-methyl-5-oxo-11-sulfino-1H-pyrrolo[2,1-c][1,4]-benzodiazepin-2-acrylamide.

13. 5,10,11,11a-Tetrahydro-10-acetyl-9-carbamyloxy-8-methyl-5-oxo-11-sulfino-1H-pyrrolo[2,1-c][1,4]-benzodiazepin-2-acrylamide.

14. 5,10,11,11a-Tetrahydro-9-hydroxy-8-methyl-5-oxo-11-sulfino-1H-pyrrolo[2,1-c][1,4]benzodiazepin-2-acrylamide.

15. 5,10,11,11a-Tetrahydro-9-acetoxy-8-methyl-5-oxo-11-sulfino-1H-pyrrolo[2,1-c][1,4]benzodiazepin-2-acrylamide.

16. 5,10,11,11a-Tetrahydro-9-carbamyloxy-8-methyl-5-oxo-11-sulfino-1H-pyrrolo[2,1-c][1,4]benzodiazepin-2-acrylamide.

17. 5,10,11,11a-Tetrahydro-8-methyl-9-methoxycarbonyloxy-5-oxo-11-sulfo-1H-pyrrolo[2,1-c][1,4]-benzodiazepin-2-acrylamide.

18. A process for producing a 1H-pyrrolo[2,1-c][1,4]-benzodiazepin-2-acrylamide compound represented by the formula

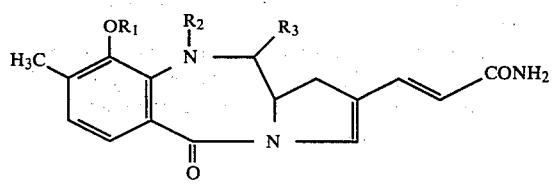

wherein $R_1$ represents a hydrogen atom, alkanoyl group having 1 to 6 carbon atoms, benzoyl group, phenylcarbamyl group, alkylcarbamyl group having 1 to 6 carbon atoms, or alkoxycarbonyl group wherein the alkoxy portion has 1 to 6 carbon atoms, $R_2$ represents a hydrogen atom, an alkanoyl group having 1 to 6 carbon atoms or a benzoyl group, and $R_3$ represents a sulfinic acid residue, $SO_2X$, wherein X is hydrogen or a pharmaceutically acceptable cation, which comprises allowing a reactive sulfur compound to react with a compound of the formula

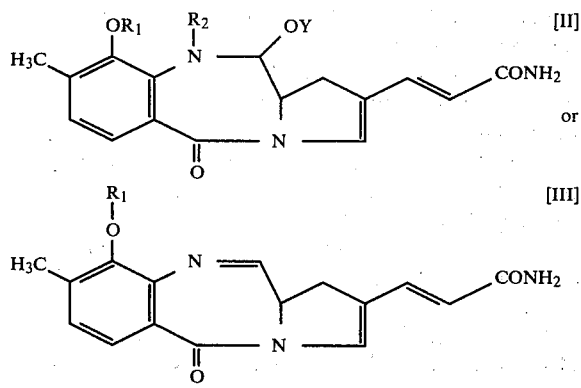

wherein $R_1$ and $R_2$ are the same as those described above and Y represents a hydrogen atom, an alkyl group or a phenyl(lower)alkyl group.

19. The process according to claim 18, wherein the reaction is carried out in an inert solvent.

20. The process according to claim 19, wherein the inert solvent is methanol, ethanol, acetone, dimethylformamide, dimethyl sulfoxide, diethyl ether, benzene hexane, a mixture thereof or a mixture with water thereof.

21. The process according to claim 18, wherein the reactive sulfur compound is disulfurous acid, trithionic acid, dithionic acid, dithionous acid, sulfurous acid, alkali metal or alkaline earth metal salts thereof or sulfur dioxide.

22. A process for producing a 1H-pyrrolo[2,1-c][1,4]-benzodiazepin-2-acrylamide compound represented by the formula

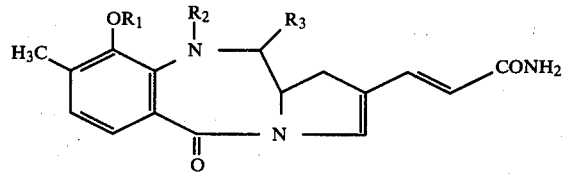

wherein $R_1$ represents a hydrogen atom, alkanoyl group having 1 to 6 carbon atoms, benzoyl group, phenylcarbamyl group, alkylcarbamyl group having 1 to 6 carbon atoms, or alkoxycarbonyl group wherein the alkoxy portion has 1 to 6 carbon atoms, $R_2$ represents a hydrogen atom, an alkanoyl group having 1 to 6 carbon atoms or a benzoyl group, and $R_3$ represents a sulfonic acid residue, $SO_3X$, wherein X is hydrogen or a pharmaceutically acceptable cation, which comprises oxidizing a compound or pharmaceutically acceptable salt thereof represented by the formula

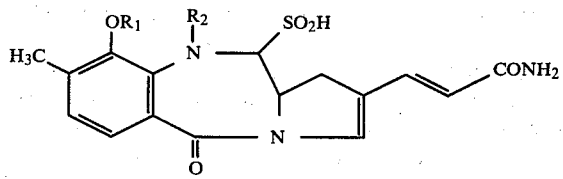

wherein $R_1$ and $R_2$ are the same as those defined above.

23. The process according to claim 22, wherein the oxidation is carried out by passing molecular oxygen containing gas through the solution of the compound or pharmaceutically acceptable salt thereof.

24. A process for producing a 1H-pyrrolo[2,1-c][1,4]benzodiazepin-2-acrylamide compound represented by the formula

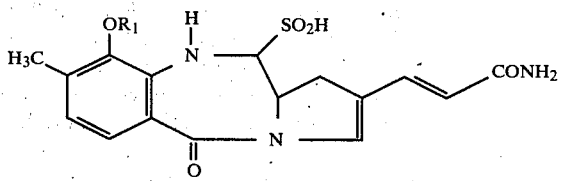

wherein $R_1$ represents a hydrogen atom, alkanoyl group having 1 to 6 carbon atoms, benzoyl group, phenylcarbamyl group, or alkoxycarbonyl group wherein the alkoxy portion has 1 to 6 carbon atoms, and a pharmaceutically acceptable salt thereof, which comprises allowing a reactive sulfur compound to react with a compound of the formula

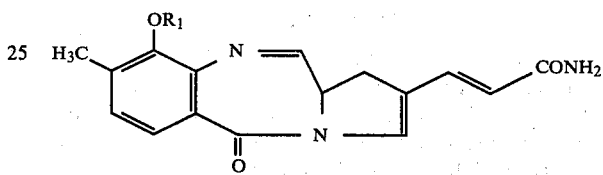

wherein $R_1$ is the same as those defined above.

25. The process according to claim 24, wherein the reaction is carried out in an inert solvent.

26. The process according to claim 25, wherein the inert solvent is methanol, ethanol, acetone, dimethylformamide, dimethylsulfoxide, diethyl ether, benzene hexane, a mixture thereof or a mixture with water thereof.

27. The process according to claim 24, wherein the reactive sulfur compound is dithionous acid, trithionic acid, dithionic acid, dithionous acid, sulfurous acid, alkali metal or alkaline earth metal salts thereof or sulfur dioxide.

28. A anti-tumer composition comprising a carrier and an anti-tumer effective amount of a 1H-pyrrolo[2,1-c][1,4]benzodiazepin-2-acrylamide compound represented by the formula

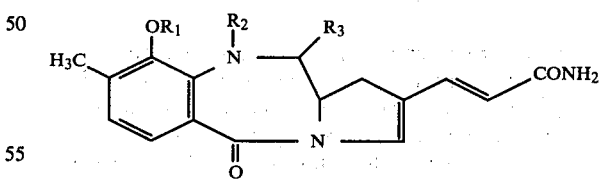

wherein $R_1$ represents a hydrogen atom, alkanoyl group having 1 to 6 carbon atoms, benzoyl group, phenylcarbamyl group, alkylcarbamyl group having 1 to 6 carbon atoms, or alkoxycarbonyl group wherein the alkoxy portion has 1 to 6 carbon atoms, $R_2$ represents a hydrogen atom, an alkanoyl group having 1 to 6 carbon atoms or a benzoyl group, and $R_3$ represents a sulfinic acid residue, $SO_2X$, or sulfonic acid residue, $SO_3X$, wherein X is hydrogen or a pharmaceutically acceptable cation.